(12) United States Patent
Eck et al.

(10) Patent No.: US 8,050,739 B2
(45) Date of Patent: Nov. 1, 2011

(54) SYSTEM AND METHOD FOR VISUALIZING HEART MORPHOLOGY DURING ELECTROPHYSIOLOGY MAPPING AND TREATMENT

(75) Inventors: Kai Eck, Aachen (DE); Alexandra Groth, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 708 days.

(21) Appl. No.: 12/095,503

(22) PCT Filed: Dec. 8, 2006

(86) PCT No.: PCT/IB2006/054716
§ 371 (c)(1),
(2), (4) Date: May 30, 2008

(87) PCT Pub. No.: WO2007/069168
PCT Pub. Date: Jun. 21, 2007

(65) Prior Publication Data
US 2010/0217116 A1 Aug. 26, 2010

Related U.S. Application Data
(60) Provisional application No. 60/750,755, filed on Dec. 15, 2005.

(51) Int. Cl.
*A61B 5/05* (2006.01)
(52) U.S. Cl. ........................ 600/424; 600/429
(58) Field of Classification Search .......... 600/407–429; 606/130
See application file for complete search history.

(56) References Cited

U.S. PATENT DOCUMENTS

| | | | |
|---|---|---|---|
| 6,226,542 B1 * | 5/2001 | Reisfeld | 600/407 |
| 6,285,898 B1 * | 9/2001 | Ben-Haim | 600/374 |
| 6,298,257 B1 * | 10/2001 | Hall et al. | 600/407 |
| 6,301,496 B1 * | 10/2001 | Reisfeld | 600/407 |
| 6,751,492 B2 * | 6/2004 | Ben-Haim | 600/374 |
| 6,915,149 B2 * | 7/2005 | Ben-Haim | 600/374 |
| 6,950,689 B1 * | 9/2005 | Willis et al. | 600/407 |
| 2001/0009974 A1 * | 7/2001 | Reisfeld | 600/407 |
| 2002/0045809 A1 * | 4/2002 | Ben-Haim | 600/374 |
| 2002/0045810 A1 * | 4/2002 | Ben-Haim | 600/374 |
| 2002/0087089 A1 * | 7/2002 | Ben-Haim | 600/509 |
| 2003/0036696 A1 * | 2/2003 | Willis et al. | 600/424 |
| 2003/0181809 A1 | 9/2003 | Hall et al. | |
| 2005/0004454 A1 | 1/2005 | Mitschke et al. | |
| 2005/0203375 A1 * | 9/2005 | Willis et al. | 600/407 |
| 2008/0221435 A1 * | 9/2008 | Rasche | 600/424 |

FOREIGN PATENT DOCUMENTS

| | | |
|---|---|---|
| WO | WO0016684 | 3/2000 |
| WO | WO2005004724 A1 | 1/2005 |
| WO | WO2005077293 A2 | 8/2005 |

* cited by examiner

*Primary Examiner* — Sanjay Cattungal (57) ABSTRACT

Systems and methods for facilitating visual detection of one or more catheter tips in relation to the morphology of an anatomical structure include locating reference catheters relative to heart tissue using an automated navigation support that draws upon prominent image features that are visible in the x-ray fluoroscopy images. The prominent features include catheter tips of reference catheters that are placed at known standard positions in relation to the anatomical structures. Based on the noted prominent features, the systems and methods achieve alignment of the anatomical structures, e.g., the heart morphology, with the interventional devices, e.g., ablation catheter(s) introduced by the physician, and generate a fused or overlaid image.

19 Claims, 5 Drawing Sheets

SYSTEM AND METHOD FOR VISUALIZING HEART MORPHOLOGY DURING ELECTROPHYSIOLOGY MAPPING AND TREATMENT

CROSS REFERENCE TO RELATED APPLICATIONS

This application claims the benefit of International Application Number PCT/IB2006/054716, filed Dec. 8, 2006, and U.S. Provisional Application Ser. No. 60/750,755 filed Dec. 15, 2005 which are incorporated herein in whole by reference.

The present disclosure relates generally to a method, system and computer software product for visualizing heart morphology during electrophysiology to identify a location of a mapping and/or ablating catheter relative to points on the cardiac tissue in real-time, in order to identify the location of the catheter in the treatment of tachycardia, for example, in relation to the cardiac morphology of the patient.

Tachycardia can be caused by abnormal conduction of the electric pulse, where the pulse doesn't follow its physiological pathway but creates feedback loops, e.g., from one of the ventricles back to the atrium (reentry tachycardia) or by non-physiologic circular conduction pathways in one of the ventricles, e.g., around scar tissue or in one of the atria, resulting in a high heart rate. A ring or line ablation is generally required to block reentry tachycardia or abnormal conduction pathways, and elimination of ablation path gaps is required.

Electrophysiologic (EP) diagnosis and treatment of cardiac arrhythmia is receiving increased levels of clinical attention. Tachycardia (irregular increases of the pulse rate with irregular heart beat configuration) requires treatment because it has been identified as a major source for small blood coagulations that induce a high risk of stroke or cardiac infarction. Sources of tachycardia can be either ectotopic (local diseased heart tissue that creates false impulses) or due to reentry conduction where the electric pulse does not follow its physiologic pathways but creates parasitic feedback loops that result in a pathologically high heart rate.

Cardiac mapping is used to locate aberrant electrical pathways and currents within the heart, as well as to diagnose mechanical and other aspects of cardiac activity. Various methods and devices have been described for mapping the heart. Radiofrequency (RF) ablation is used to treat cardiac arrhythmia by ablating and killing cardiac tissue in order to create non-conducting lesions that disrupt the abnormal electrical pathway causing the arrhythmia. In RF ablation, heat is induced at the tip of an ablation catheter to create lesions in the myocardium. Such ablated scar tissue can no longer create or transport electric impulses. Local ablation destroys irregular local sources, whereas a ring or line ablation is required to block reentry tachycardia.

Figure 1:
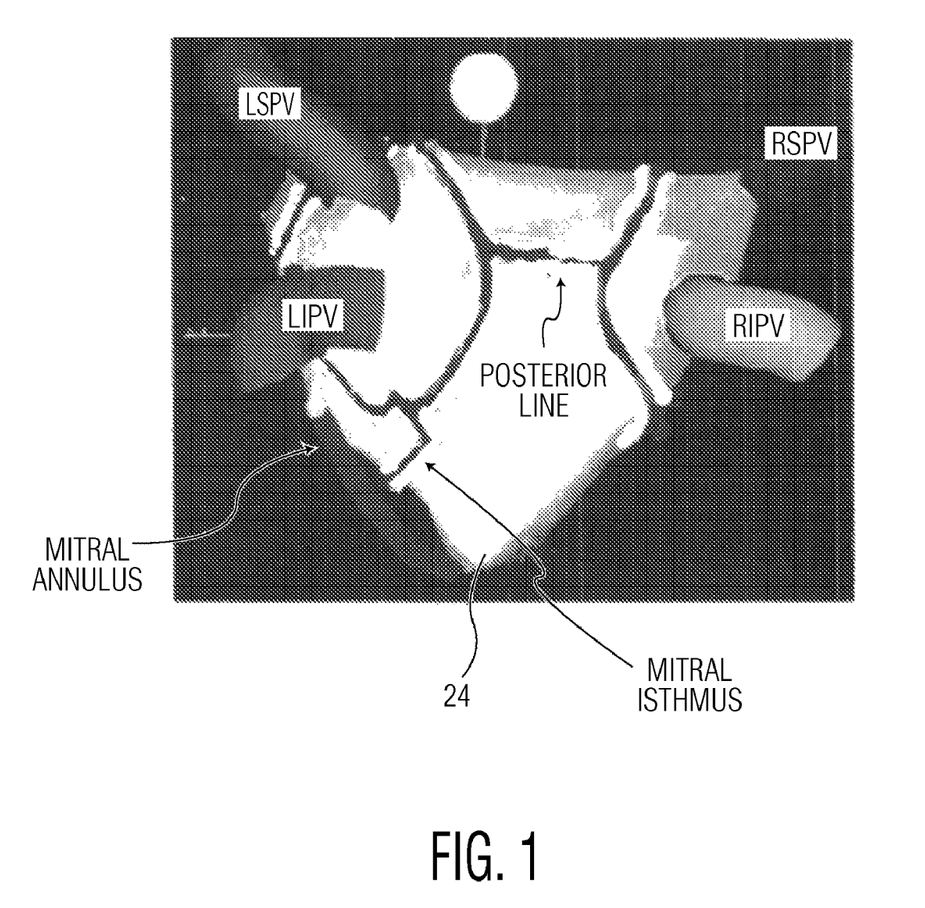
FIG. 1 depicts an intended ablation path on a so-called cartoon image of the left atrium of a patient's heart.

FIG. 1 depicts what is commonly referred to as a cartoon image of localizer information relating to an ablation procedure in the left atrium of a patient's heart 24. The line traversing and forming rings about the heart tissue indicate positions where an ablation-induced block was intended by the physician.

In electrophysiological (EP) procedures, the position of the mapping and/or ablating catheter is often difficult to identify in relation to the patient's heart morphology. In the current state-of-the-art, the physician generally judges the position of the heart in relation to the catheters from faint shadows of the heart or from the position of the reference catheters that are visible on x-ray projection images. Alternatively, the physician may use a localizer system (e.g., CARTO from Biosense Webster, NavX from Ensight, etc.) that relates the position of the catheter to some reference coordinate system, but not necessarily to the anatomy of the patient. Even with localizers on the catheter, physicians often use fluoroscopy in an effort to verify the estimated position provided by the localizer system.

It has been proposed to overlay segmented heart anatomy outlines on top of an x-ray fluoroscopy image to indicate an estimated position of the catheter(s). However, motion of the heart (e.g., based on intermittent/periodic heart contractions) creates difficulties in reliably or accurately overlaying the morphology of the patient from pre-interventional image data on the fluoroscopy images. Further, the heart also moves relative to the chest, e.g., based on diaphragm pressure. Therefore, an uncompensated overlay of the heart's morphology onto a fluoroscopy image is likely to yield poor and/or unreliable alignment of this pre-interventional volume with the actual position of the (invisible) heart.

Therefore, it would be desirable to provide a method and/or system to compensate for the motion of the heart and overlay heart anatomy outlines on x-ray fluoroscopy image(s) to facilitate clinical procedures and/or diagnosis, e.g., to indicate the location of the catheter to the physician. It would be particularly desirable to overlay segmented heart anatomy outlines on x-ray fluoroscopy image(s) to facilitate clinical procedures and/or diagnosis.

As set forth herein, the present disclosure advantageously facilitates visual detection of the catheter tip in relation to the morphology of heart tissue using an automated navigation support using prominent image features that are visible in the x-ray fluoroscopy images. According to exemplary embodiments of the present disclosure, prominent features of potential utility include one or more catheter tips of reference catheter(s) that are typically placed at known standard positions in relation to heart morphology. Based on the noted prominent features, the systems and methods of the present disclosure are effective in achieving alignment of the anatomical structures, e.g., the heart morphology, with the interventional devices, e.g., ablation catheter(s) introduced by the physician.

The systems and methods of the present disclosure may be advantageously employed in electrophysiological interventions, which typically taking place in a Cathlab under fluoroscopic x-ray control. The disclosed systems and methods have particular utility for cardiology applications, including mapping and/or ablation of heart tissue. By accurately and reliably overlaying the heart morphology onto a real-time fluoroscopy image, the physician/clinician realizes several clinical advantages, e.g., a reduction in the amount of time/effort that is spent in trial and error corrections of incomplete ring and line ablations to treat reentry tachycardia.

Additional features, functions and advantages associated with the disclosed method, system and computer software product will be apparent from the detailed description which follows, particularly when reviewed in conjunction with the figures appended hereto.

To assist those of ordinary skill in the art in making and using the disclosed method, system and computer software product, reference is made to the appended figures, wherein.

Figure 2:
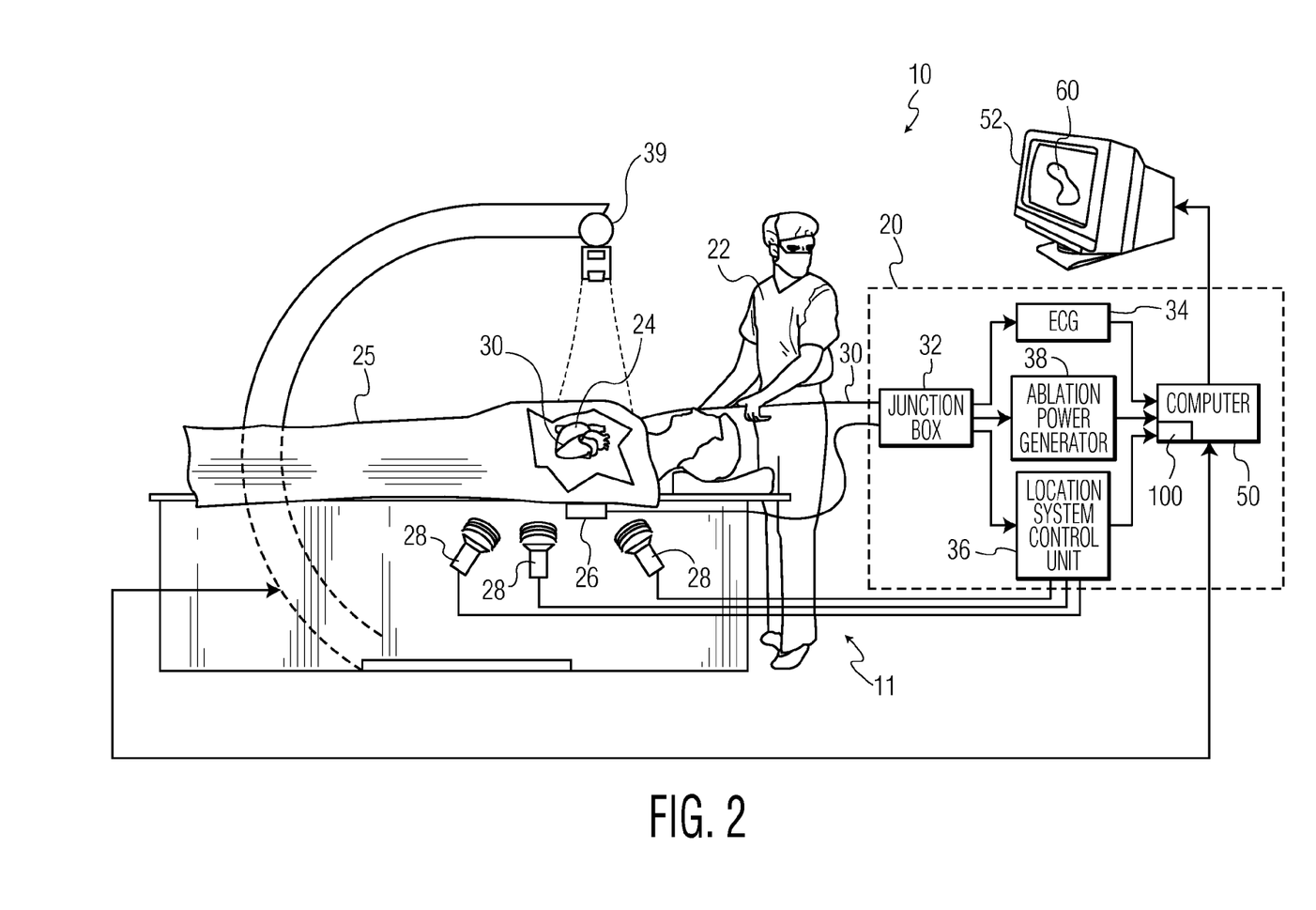
FIG. 2 is a schematic, pictorial illustration of a system for real-time mapping of cardiac ablation treatment in the heart, in accordance with an exemplary embodiment of the present disclosure.

With initial reference to FIG. 2, a schematic, pictorial illustration of a mapping system 10 for real-time mapping in connection with a clinical or diagnostic procedure, e.g., a cardiac ablation treatment in a heart 24 of a subject 25, is provided in accordance with an exemplary embodiment of the present disclosure. System 10 includes at least one interventional device, e.g., an elongated mapping probe, preferably a catheter 30, which is inserted by a user 22 through a vein or artery of the subject into a desired clinical/anatomical location, e.g., a chamber of the heart, which can be the right or left ventricle or atrium. Techniques for catheter introduction are well known to persons skilled in the art.

Figure 3:
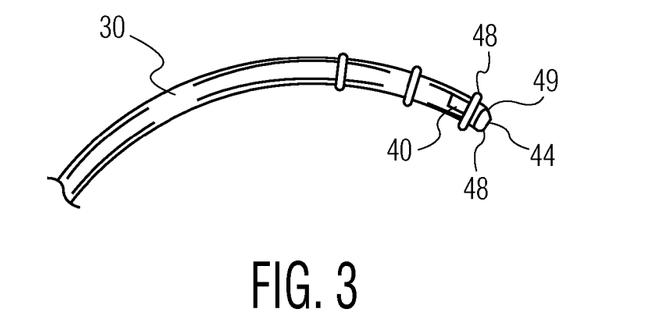
FIG. 3 is a schematic, pictorial illustration of a distal portion of an exemplary catheter used in the system of FIG. 2, in accordance with an exemplary embodiment of the present disclosure.

FIG. 3 is a schematic, pictorial illustration showing a distal portion of an exemplary catheter 30. As noted previously, catheter is fed through the patient's venous system for insertion/positioning in heart 24. Catheter 30 preferably includes at least one position sensor 40, a tip electrode 48, and one or more temperature sensors 49, all of which are preferably fixed at or near a distal tip 44 of the catheter. Temperature sensors 49 may include, for example, one or more thermocouples and/or thermistors. Position sensor 40 generally generates or receives signals used to determine the position and orientation of catheter 30 within the patient's anatomy, e.g., within a chamber of the heart.

In exemplary catheter 30, tip electrode 48 is generally configured to apply electrical signals to heart 24 for ablating cardiac tissue, and may preferably be further configured for diagnostic purposes, such as cardiac mapping. Alternatively, separate electrodes may be provided for diagnostic purposes and for ablating cardiac tissue. According to exemplary embodiments of the present disclosure, a fixed positional and orientational relationship may be established between position sensor 40, distal tip 44 and tip electrode 48. Optionally, catheter 30 may further include at least one additional position sensor (not shown) and/or radio-opaque markers (see elements 308 in FIG. 5) to identify individual catheters and to determine their location and orientation on x-ray projection images, as described herein.

With further reference to FIG. 2, in an exemplary implementation of the present disclosure, mapping system 10 includes a display monitor 52, an imaging system 39 and a console 20. A location system control unit 36, an ablation power generator 38, a junction box 32, an electrocardiogram (ECG) recording and/or monitoring system 34 and a computer 50 are typically included with system 10, e.g., in conjunction (in whole or in part) with console 20. Computer 50 generally includes appropriate processing capabilities and/or signal processing circuits that are adapted to perform the signal processing functionalities described herein. Although it is contemplated that computer 50 will perform the requisite processing functions locally, it is further contemplated that networked computer systems, e.g., an intranet, extranet or the like, may be employed to access processing capabilities and/or programming and/or data-related resources.

Thus, according to exemplary embodiments of the present disclosure, computer 50 is programmed with software and/or hardware to carry out the processing functions and communications described herein. Software may be downloaded to the computer in electronic form, over a network, for example, or such software may alternatively be provided on tangible media, such as magnetic or optical media or other non-volatile memory, for access and/or use by the processing unit(s) associated with computer 50. In some embodiments, computer 50 takes the form of a general-purpose computer.

In the exemplary embodiment of system 10, junction box 32 preferably routes (a) conducting wires and temperature sensor signals from catheter 30 to ablation power generator 38, (b) location sensor information from sensor 40 of catheter 30 to location system control unit 36, and (c) the diagnostic electrode signals generated by tip electrode 48 to ECG monitor 34. Alternatively or additionally, junction box 32 may route one or more of these signals directly to computer 50 (and, by extension, to an associated network). ECG monitor 34 is preferably also coupled to receive signals from one or more body surface electrodes, so as to provide an ECG synchronization signal to the processing unit(s) associated with computer 50.

The imaging system 39 is further operably connected to computer 50 for receipt and processing of images (or imaging signals) from imaging system 39. In an exemplary embodiment, imaging system 39 is a fluoroscopy x-ray system. However, other imaging modalities are contemplated for use according to the disclosed systems and methods, including, but not limited to, MRI, echocardiography, CT, or any other modality suitable to provide an instantaneous image that captures the current position of an interventional device, e.g., a catheter, together with relevant anatomical structure(s), e.g., heart tissue.

A location system 11 is typically associated with the disclosed system and generally includes a set of external radiators 28, position sensor 40 of catheter 30, and location system control unit 36. One or more additional position sensors may be employed, as will be apparent to persons skilled in the art, and such additional position sensor(s) also typically communicate with location system 11. External radiators 28 are generally adapted to be located at respective positions external to subject 25 and to generate fields, such as electromagnetic fields, that are sensed by position sensor 40. Thus, position sensor 40 is advantageously adapted to detect the fields generated by radiators 28 and, based on the sensed field data, facilitate a calculation of the position coordinates of position sensor 40 by location system control unit 36. Alternatively, position sensor 40 may be configured and adapted to generate fields, which are in turn detected by external radiators 28.

For some exemplary applications of the disclosed systems and methods, a reference position sensor, typically either on an externally-applied reference patch attached to the exterior of the body of the subject, or on an internally-placed catheter, is maintained in a generally fixed position relative to an anatomical structure, e.g., heart 24. By comparing the position of catheter 30 to that of the reference catheter, the coordinates of catheter 30 are accurately determined relative to the anatomical structure, e.g., the heart, irrespective of the potential relative motion of such anatomical structure. Indeed, in an exemplary embodiment of the present disclosure, ECG 34 and an additional respiration sensor function to generate data that is used to generate heartbeat and respiration motion compensation, as discussed further below.

Location system control unit 36 receives signals from position sensor 40 (or from external radiators 28 when position sensor 40 generates the energy fields), calculates the location of sensor 40 and catheter 30, and transmits to computer 50 the location information and energy dose information (received from ablation power generator 38, as described below) which relates to the location information. The location system control unit 36 preferably generates and transmits location information (and energy dose information) essentially continuously during a clinical or diagnostic procedure.

Ablation power generator 38 preferably generates power used by tip electrode 48 to perform ablation. Preferably, the ablation power generator generates RF power for performing RF ablation. Alternatively or additionally, the ablation power generator induces ablation by means of other ablation techniques, such as laser ablation or ultrasound ablation, for example. Preferably, suitable feedback techniques are applied to facilitate identifying less than suitable ablated regions on the cardiac map, as discussed more fully below.

According to exemplary embodiments of the present disclosure, ablation power generator 38 includes a feedback system that allows the delivery of appropriate current levels to maintain the tip at a constant temperature of between about 50° C. to about 65° C. The ablation power generator 38 typically transmits electrical current information related to the current needed to maintain a constant tip temperature to computer 50, e.g., over a serial communications line. The ablation power generator preferably measures and transmits the sustaining electrical current level, i.e., the current level required to maintain the ablation tip in the desired temperature range, on an essentially continuous basis.

Alternatively, a cardiac map generated during a previous cardiac procedure may be used according to the present disclosure. In an exemplary embodiment, a cardiac map adapted to the patient heart's anatomy is acquired from another source, such as an imaging modality (e.g., fluoroscopy, MRI, echocardiography, CT, single-photon computed tomography (SPECT), or positron emission tomography (PET)), and the location of the catheter may be visualized on an image of a transformed pre-interventional data volume set defining the cardiac map fused/overlaid with a real-time x-ray image, as discussed more fully below.

Figure 4:
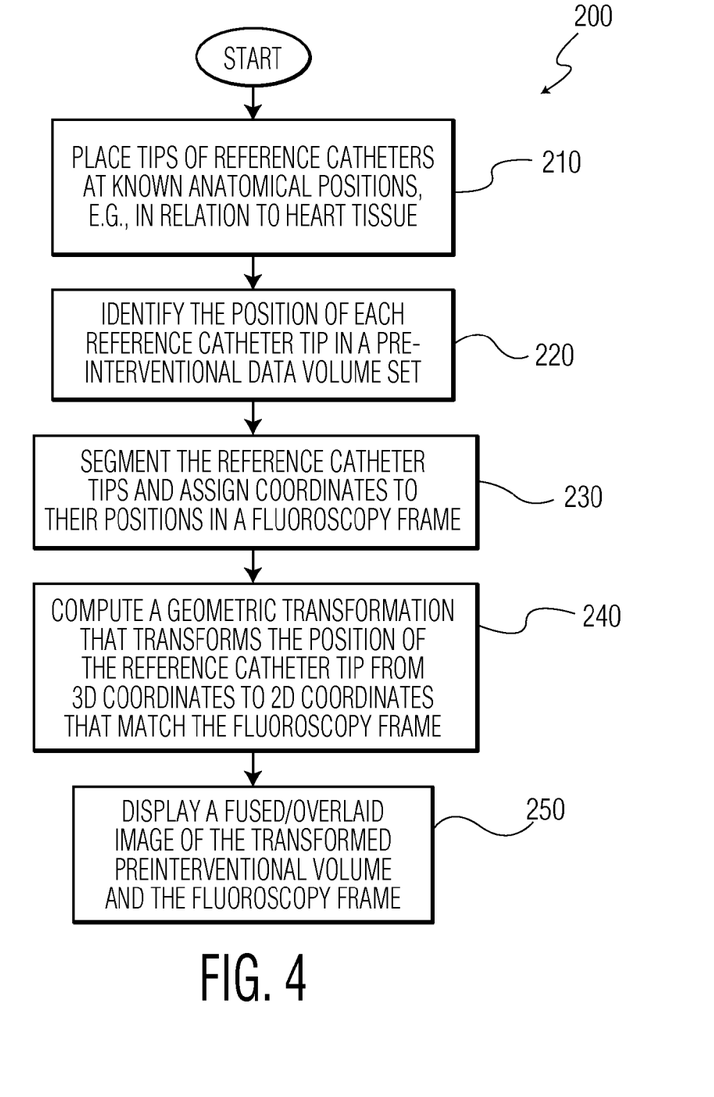
FIG. 4 is a flow chart that schematically illustrates a method for determining a catheter position in relation to a region of interest (e.g., cardiac chamber) of a patient, in accordance with an exemplary embodiment of the present disclosure.

FIG. 4 is a flow chart 200 that schematically illustrates a method of determining a position of a catheter in relation to a region of interest of a patient (e.g., heart morphology) during a clinical or diagnostic procedure, e.g., an EP procedure, in accordance with an exemplary embodiment of the present disclosure. At block 210, catheter tips 44 corresponding to a plurality of reference catheters are each placed at a known anatomical position, e.g., relative to heart tissue. In cardiology applications, the catheter tips 44 of the reference catheters are generally placed at known standard positions inside the heart, as these tips 44 are visible in the fluoroscopy images. The alignment of the volume to the anatomical structure, e.g., the (invisible) heart, is initiated at block 220, where the respective positions of each of the plurality of reference catheter tips 44 are identified in a pre-interventional data volume (once). The pre-interventional data volume is derived from a previously acquired image, e.g., based on 3-D CT scan or MRI imaging procedure.

After straightforward pre-processing of x-ray fluoroscopic images (background removal either by morphological filtering or sliding time maximum subtraction), the pre-processed image is correlated with a filter that represents the catheter tip 44 and the nearby-located markers. This filter is chosen either a priori or derived from an undisturbed 'pure' x-ray projection image of the catheter, which was acquired prior to the intervention-of-interest. Local maxima of the correlation result are accounted as marker and tip candidates.

Since the tips 44 and markers are usually arranged in a line, all pairs of candidates that are neither too far apart (e.g., cannot belong to one line of markers) and that are neither too near (e.g., unstable estimation due to foreshortening) are Hough-transformed, meaning that the corresponding line though the two candidates is represented in the Hough-domain. The respective entries in the Hough domain form a circular-distributed cluster which permits discrimination between two marker lines essentially at the same position that have different orientations.

The clustering in Hough-domain is typically undertaken using a conventional k-means algorithm, but can also be undertaken using other textbook clustering methods. Once the clusters are recognized, the end points of the candidates forming one line are identified and tested regarding their isotropy. The catheter tip 44 is much more anisotropic than the first marker of the catheter and can thereby be easily identified. Alternatively or in addition, the orientation of the line and the relative position of the tip 44 can be propagated from previous images.

At block 230, the positions of the reference catheter tips 44 are segmented and assigned coordinates for their respective positions in an x-ray fluoroscopic frame image (real-time). The pre-interventional volume data set (e.g., from a prior MRI or CT imaging procedure) is segmented using an annotated model. These annotations contain all common positions of the reference catheters. In the process of segmentation, the model is deformed to match the measured data and the annotated points are automatically moved to the respective positions in the patient data set. Alternatively, the aimed reference catheter positions can be marked in the volume data set by the physician, clinician or other clinical personnel.

At block 240, a geometric transformation is computed that transforms the respective positions of the reference catheter tips 44 from 3-D coordinates in a manner that a projection through the volume transforms the 3-D coordinates to 2-D coordinates that match the fluoroscopy frame (real-time). An easy implementation of this principle relies on the condition that only a rigid transformation of one static segmentation result of the patient's anatomical structure (e.g., heart morphology) is possible to match the estimated reference catheter positions. To avoid artifacts due to anatomical motion, e.g., based on heart beat motion, the catheter motion is low-pass filtered.

More elaborate schemes may use a 4-D (e.g., 3-D+time) model of the anatomical structure, e.g., the heart, derived from a number of reconstructions of the anatomical structure, e.g., the heart in different contraction states. In this case, the ECG signal gives the right contraction status and the respective model is then fitted using a rigid transformation.

At block 250, a fused or overlaid image of the transformed pre-interventional data volume and the fluroscopy frame are displayed on the monitor 52. In this manner, the user, clinician and/or interventionalist 22 can verify the location of the catheter of interest relative to the anatomy of the patient (e.g., 2-D heart morphology), rather than relating its position to some coordinate system used by a localizer system. The fused or overlaid image data may be printed out, stored on disk, or otherwise retained for future reference by hospital staff, as appropriate.

Figure 5:
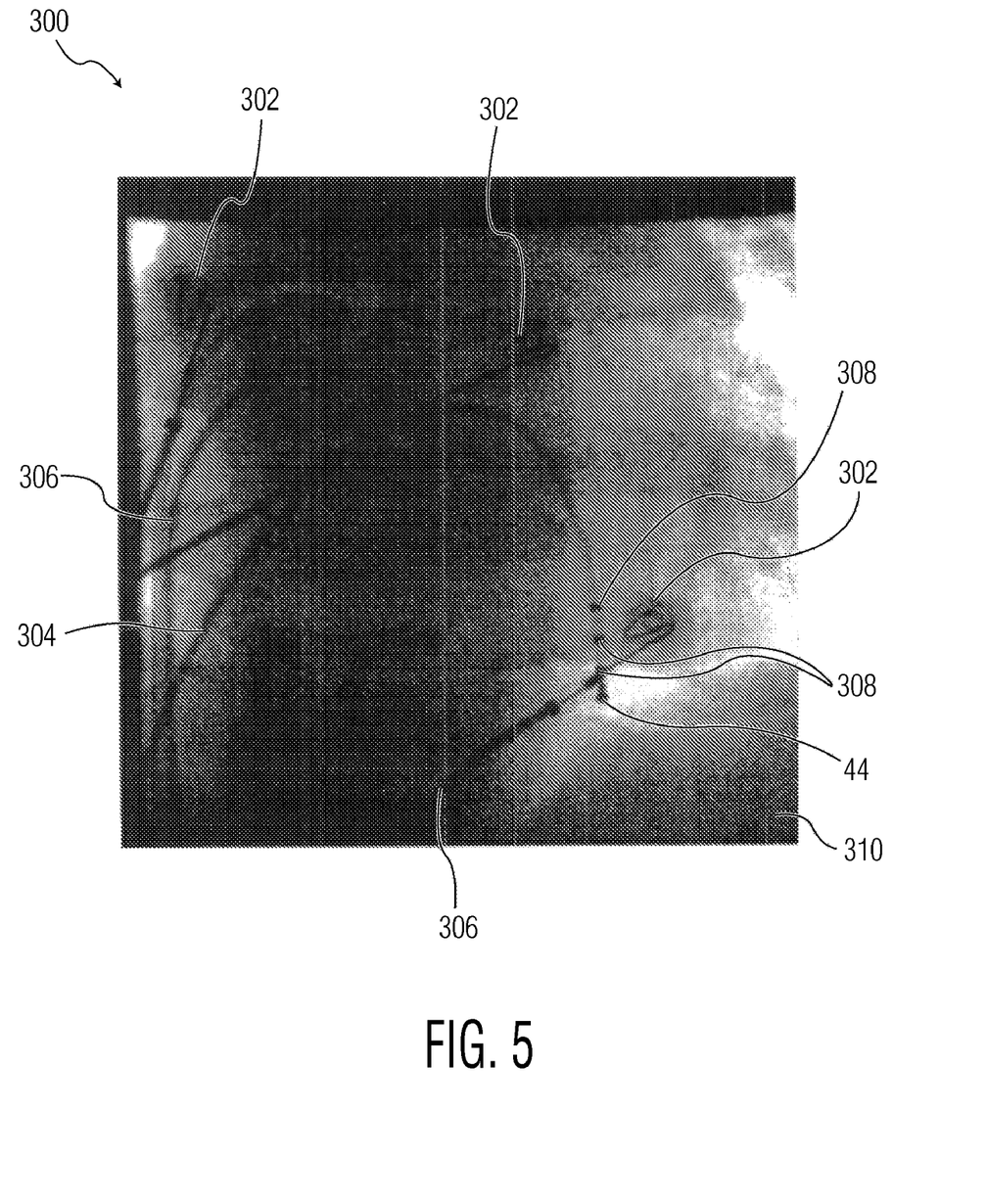
FIG. 5 illustrates a visualization of an x-ray fluoroscopy image with a plurality of catheter tips positioned relative to a patient's anatomical structures.

In exemplary embodiments of the present disclosure, segmented heart anatomy outlines are overlaid on top of a fluoroscopic x-ray image to give the user, clinician or interventionalist 22 a better indication of where the catheter of interest is located relative to the anatomy of the patient (e.g., heart). FIG. 5 is a fluoroscopic image 300 before the overlaying or fusing segmented heart anatomy outlines with the fluoroscopic image 300. Image 300 illustrates a plurality of ECG leads 302 proximate heart 24 attached to the patient's skin. The reference EP catheter 304 in one of the atria is the middle one of the three visible catheters 306, i.e. the dark bend structures. This catheter 304 is positioned at an anatomical landmark, e.g. the coronary sinus. The lower EP catheter 306 appears to lay in the left ventricle close to the apex. On this catheter, radio-opaque marker rings 308 are easily visible. The upper catheter 306, as illustrated, is located in one of the atrial chambers of the heart. The diaphragm 310 separating the lung from abdominal organs is visible in the lower right of the image 300 and is a possible source to determine the depth of respiration intake, which causes the heart to move along a longitudinal axis defining the body of the patient. Image 300 illustrates the arc-shaped transition from bright lung tissue to darker abdominal tissue. Furthermore, image 300 depicts the spine and some ribs, but these are not of interest for purposes of the present disclosure.

Figure 6:
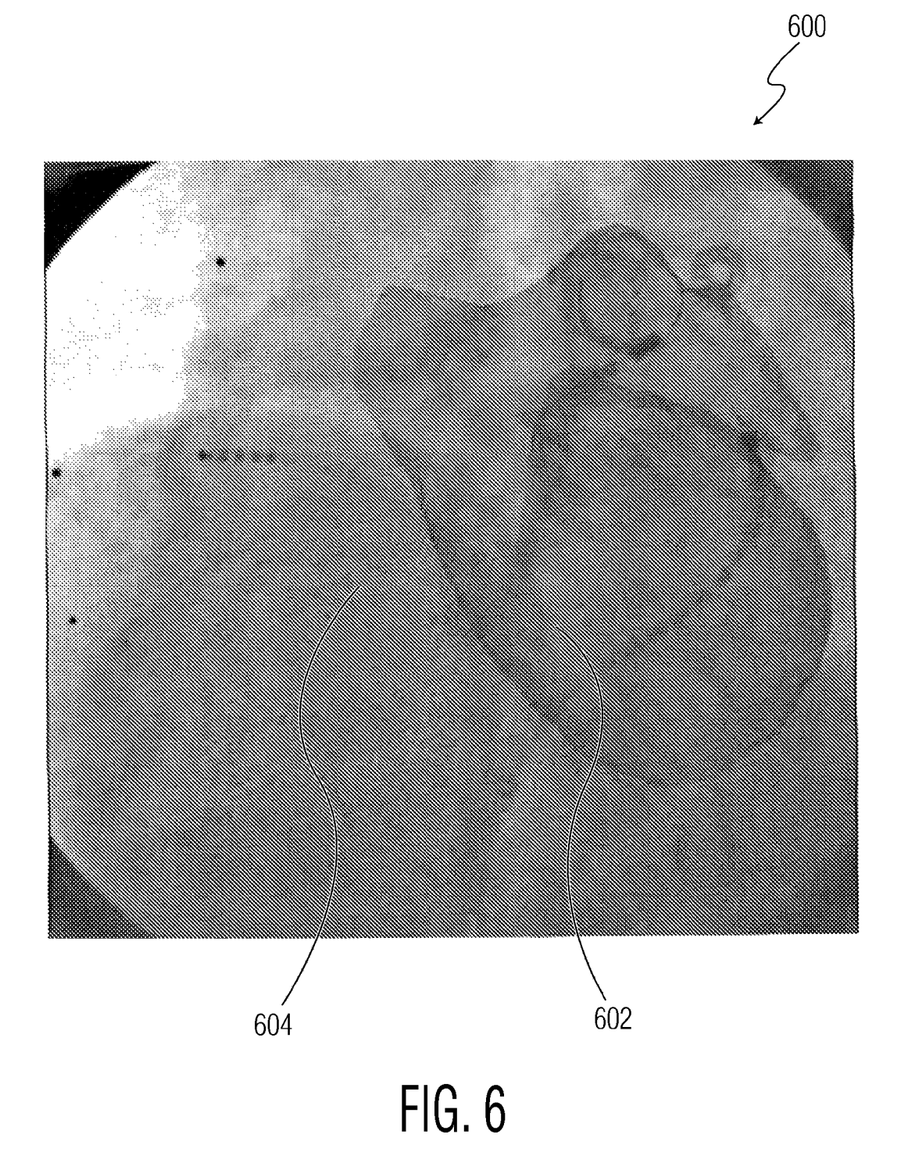
FIG. 6 illustrates a fused visualization of a transformed pre-interventional volume overlaid on an x-ray fluoroscopy image visually locating a catheter tip in relation to heart tissue, in accordance with an exemplary embodiment of the present disclosure.

By use of mask overlays, i.e. a mixing of a transformed pre-interventional data volume and real-time acquisition of a fluoroscopic x-ray image, the current position of the catheter relative to the heart morphology can be presented such that guidance of the catheter to a region of interest is guided by a real-time image of the heart anatomy and, therefore, easily achievable. Thus, with reference to FIG. 6, an exemplary fused or overlaid image 600 of heart morphology 602 that is overlaid on a fluoroscopic image 604 is provided. As is readily apparent from the exemplary fused or overlaid image 600 of FIG. 6, a clinician or other system user is better equipped to perform clinical and/or diagnostic procedures when provided to the combined fluoroscopic and anatomical images provided by the disclosed systems and methods.

Referring again to FIG. 2, one proposed embodiment of the invention includes a software module that is integrated into a workstation or console 20, e.g., an EP workstation, depicted generally at 100 within computer 50. Such a workstation generally functions as the central control and display unit for a clinical or diagnostic procedure, e.g., an EP procedure, and is adapted to combine the EP-specific ECG signals, x-ray and localizer information. The software module 100 receives the pre-interventional data volume set of the anatomical structure-of-interest, e.g., the heart morphology, to align the anatomical structure, e.g., the invisible heart, of the x-ray image therewith in order to visualize the anatomical structure, e.g., the heart during EP mapping and treatment. The software module 100 instructs computer 50 to automatically identify positions of the reference catheters in the pre-interventional data volume set (once). The software module 100 further instructs computer 50 to automatically segment the reference catheter tips and assign respective coordinates to their positions in the x-ray fluoroscopy frame (real-time). The software module 100 thereafter instructs computer 50 to automatically compute a geometric transformation that transforms the 3-D coordinate positions of the reference catheters, such that a projection through the volume results in 2-D coordinates that match those of the fluoroscopy (real-time). After performing these steps, the software module 100 instructs computer 50 to display a fused or overlaid image of the pre-interventional data volume set and the x-ray image.

The potential for advanced and dedicated EP lab equipment incorporating the software module 100 offers significant clinical and diagnostic benefits. For example, the compensated overlay of the morphology of the heart from a pre-interventional data volume results in alignment with the actual position of the (invisible) heart in real time fluoroscopy images. One advantage of this overlay includes positioning verification of the catheter-of-interest in real-time during EP mapping and cardiovascular treatments.

Any dedicated EP lab may incorporate the EP workstation according to the exemplary embodiments described herein, e.g., a target hardware that controls and combines the various hardware (e.g., x-ray imager, EP ECG acquisition, ablation catheter control, and localizer system). The invention is also easily included in a software package for such workstations, e.g., as an accessory module or the like.

In sum, the disclosed, system, method, and computer software product provide significant benefits to clinicians and healthcare personnel involved in diagnostic procedures, particularly physicians desiring a reduction in the amount of time to verify the location of a catheter-of-interest in relation to actual anatomical structure(s), e.g., heart morphology visualized during x-ray fluoroscopy. Further, the overlay of a compensated pre-interventional data volume is simplified when heartbeat and/or respiration motion compensation is provided using an ECG and information on depth of respiration. In this manner, the location of the catheter-of-interest can be accurately visualized at any time during the cardiac and/or respiration cycle. In contrast, the current use of the localizer information provides the position of the catheter relative to some reference coordinate system, but not necessarily to the anatomy of the patient.

Advantageously, embodiments of the present disclosure enable users of the system, method and computer software to visually determine, in real-time during a procedure, the position of a catheter-of-interest in relation to a 2-D representation of the morphology of the heart overlaid on an x-ray fluoroscopic image. As a result, positional verification of the catheter-of-interest is discerned more quickly, thus allowing a more complete non-conducting lesion to be typically formed, without unnecessary ablation of excess cardiac tissue, for example.

Although the method, system and software product of the present disclosure have been described with reference to exemplary embodiments thereof, the present disclosure is not limited to such exemplary embodiments. Rather, the method, system and software product disclosed herein are susceptible to a variety of modifications, enhancements and/or variations, without departing from the spirit or scope hereof. For example, the disclosed systems and methods may find particular utility in a variety of clinical and diagnostic settings, e.g., procedures for injecting and/or placing stem cells and stem cell-containing treatments in vivo. Accordingly, the present disclosure embodies and encompasses such modifications, enhancements and/or variations within the scope of the claims appended hereto.

The invention claimed is:

1. A method of determining a position of a catheter in relation to a region of interest of a patient during an interventional procedure, the method comprising the acts of:

placing catheter tips, each tip of the catheter tips corresponding to one of a plurality of reference catheters, at a known position within the body of the patient;

identifying positions of a respective position of each of the plurality of reference catheter tips in a pre-interventional data volume obtained from previous images of the region of interest of the patient prior to the interventional procedure;

segmenting the plurality of reference catheter tips in the pre-interventional data volume to form segmented tips;

assigning coordinates to each position of the segmented tips in an x-ray image obtained during the interventional procedure;

computing by a processor a geometric transformation that transforms the identified positions of each of the segmented tips in the pre-interventional data volume given as 3-D coordinates in a manner that a projection through the volume results in 2-D coordinates that correspond to a 2-D coordinates that match obtained positions obtained from the x-ray image obtained during the interventional procedure; and displaying one of a fused or overlaid image of the pre-interventional data volume and the x-ray image to verify the location of the catheter in relation to a morphology of the patient.

2. The method of claim 1, wherein the x-ray image is a fluoroscopy image.

3. The method of claim 1, wherein the previous images are acquired by at least one of 3-D CT scan and an MRI scan.

4. The method of claim 1, wherein the segmenting and assigning acts includes using an annotated model to form annotated points at positions of the segmented tips.

5. The method of claim 4, wherein the annotated model includes all common positions of the plurality of reference catheters.

6. The method of claim 4, wherein using the annotated model includes the acts of:
deforming the annotated model to match the obtained positions obtained during the interventional procedure; and
moving the annotated points to respective positions in a patient data set.

7. The method of claim 1, wherein the identifying includes marking the positions in the pre-interventional data volume by a user.

8. The method of claim 1, wherein the computing act includes a rigid transformation of one static segmentation result of the morphology of the region of interest of the patient to match an estimated position of each of the plurality of reference catheters.

9. The method of claim 1, wherein the region of interest includes morphology of the heart.

10. The method of claim 1, wherein the geometric transformation includes a rigid transformation to correspond to at least one of depth of respiration intake and phase in the cardiac cycle using information from an electrocardiogram and respiration sensor, respectively, with respect to motion of the catheter due to heart beat and respiration, respectively.

11. The method of claim 1, wherein the interventional procedure comprises an electrophysiologic procedure.

12. An imaging system for imaging a region of interest of the body and visualizing a catheter of interest, the system comprising:

a catheter of interest configured for at least one of mapping and ablation;

a plurality of reference catheters, each having a catheter tip placed at known position of the region of interest of the body;

an image processing unit coupled to the catheter of interest and the plurality of reference catheters and configured to:

identify positions of a respective position of each of the plurality of reference catheter tips in a pre-interventional data volume obtained from previous images of the region of interest of the patient prior to the interventional procedure, segment the plurality of reference catheter tips in the pre-interventional data volume to form segmented tips, assign coordinates to each of position of the segmented tips in an x-ray image obtained during the interventional procedure, and compute a geometric transformation that transforms the identified positions of each of the segmented tips in the pre-interventional data volume given as 3-D coordinates in a manner that a projection through the volume results in 2-D coordinates that correspond to a 2-D coordinates that match obtained positions obtained from the x-ray image obtained during the interventional procedure; and a display means coupled to the image processing unit to display one of a fused or overlaid image of the pre-interventional data volume and the x-ray image to verify the location of the catheter in relation to a morphology of the patient.

13. The system of claim 12, wherein the x-ray image is a fluoroscopy image.

14. The system of claim 12, wherein the previous images are acquired by at least one of 3-D CT scan and an MRI image scan.

15. The system of claim 12, wherein the region of interest includes morphology of the heart.

16. A tangible computer readable medium embodying non-transitory computer instructions for determining a position of a catheter in relation to a region of interest of a patient during an interventional procedure, the non-transitory computer instructions being operative, when read by a computer, cause the computer to:

identify positions of a respective position of each of a plurality of reference catheter tips in a pre-interventional data volume obtained from previous images of the region of interest of the patient prior to the interventional procedure, each catheter tip being placed at known position of the region of interest of the patient;

segment the plurality of reference catheter tips in the pre-interventional data volume to form segmented tips;

assign coordinates to each position of the segmented tips in an x-ray image obtained during the interventional procedure;

compute a geometric transformation that transforms the identified positions of each of the segmented tips in the pre-interventional data volume given as 3-D coordinates in a manner that a projection through the volume results in 2-D coordinates that correspond to a 2-D coordinates that match obtained positions obtained from the x-ray image obtained during the interventional procedure; and display one of a fused or overlaid image of the pre-interventional data volume and the x-ray image to verify the location of the catheter in relation to a morphology of the patient.

17. The tangible computer readable medium of claim 16, wherein the x-ray image is a fluoroscopy image.

18. The tangible computer readable medium of claim 16, wherein the pre-interventional data volume is derived from at least one of a previously acquired 3-D CT scan and a MRI image.

19. The tangible computer readable medium claim 16, wherein the region of interest includes morphology of the heart.

* * * * *